US011452997B2

(12) United States Patent
Dakka et al.

(10) Patent No.: US 11,452,997 B2
(45) Date of Patent: Sep. 27, 2022

(54) OLIGOMERIZATION OF ISOBUTANOL IN THE PRESENCE OF MWW ZEOLITE SOLID ACID CATALYSTS

(71) Applicant: ExxonMobil Technology and Engineering Company, Annandale, NJ (US)

(72) Inventors: Jihad M Dakka, Whitehouse Station, NJ (US); Patrick L Hanks, Bridgewater, NJ (US); Brandon M Carcuffe, Hackettstown, NJ (US); Cynthia F Omilian, Annandale, NJ (US); Ralph C DeHaas, Easton, PA (US); Arsam Behkish, Flemington, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 64 days.

(21) Appl. No.: 17/136,553

(22) Filed: Dec. 29, 2020

(65) Prior Publication Data
US 2021/0229081 A1    Jul. 29, 2021

Related U.S. Application Data

(60) Provisional application No. 62/967,190, filed on Jan. 29, 2020.

(51) Int. Cl.
*C07C 1/24*    (2006.01)
*C07C 1/20*    (2006.01)
(Continued)

(52) U.S. Cl.
CPC ............. *B01J 29/7038* (2013.01); *C07C 1/24* (2013.01); *C07C 5/13* (2013.01); *C10G 49/08* (2013.01);
(Continued)

(58) Field of Classification Search
CPC .......... B01J 29/7038; C07C 1/24; C07C 5/13; C07C 9/15; C07C 9/16; C07C 2529/70;
(Continued)

(56) References Cited

U.S. PATENT DOCUMENTS

2011/0282120 A1*  11/2011  Buchanan ............... C07C 37/08
                                                    585/329
2013/0204058 A1*  8/2013  Adam ..................... C12P 5/026
                                                    585/329

(Continued)

FOREIGN PATENT DOCUMENTS

EP        3162763 A1    5/2017

OTHER PUBLICATIONS

The International Search Report and Written Opinion of PCT/US2020/067299 dated Apr. 13, 2021.

*Primary Examiner* — In Suk C Bullock
*Assistant Examiner* — Jason Y Chong
(74) *Attorney, Agent, or Firm* — Kristina Okafor

(57) ABSTRACT

Isobutanol may be converted into predominantly $C_{12+}$ olefin oligomers under specified conditions. Such methods may comprise: contacting a feed comprising isobutanol with a zeolite solid acid catalyst having a MWW framework under conditions effective to convert the isobutanol into a product comprising $C_{4n}$ olefin oligomers, wherein n is an integer having a value of two or greater and about 80 wt. % or greater of the $C_{4n}$ olefin oligomers are larger than $C_8$.

20 Claims, 9 Drawing Sheets

(51) Int. Cl.
  *B01J 29/70* (2006.01)
  *C07C 5/13* (2006.01)
  *C10G 49/08* (2006.01)
  *C07C 9/15* (2006.01)
  *C07C 9/16* (2006.01)

(52) U.S. Cl.
  CPC .................. *C07C 9/15* (2013.01); *C07C 9/16* (2013.01); *C10G 2300/1092* (2013.01); *C10G 2300/4018* (2013.01); *C10G 2300/70* (2013.01); *C10G 2400/08* (2013.01)

(58) Field of Classification Search
  CPC ............ C10G 49/08; C10G 2300/1092; C10G 2300/4018; C10G 2300/70; C10G 2400/08
  See application file for complete search history.

(56) References Cited

U.S. PATENT DOCUMENTS

| | | | |
|---|---|---|---|
| 2015/0376089 A1* | 12/2015 | Fichtl | C07C 2/12 422/187 |
| 2018/0162788 A1 | 6/2018 | Dakka et al. | |
| 2018/0201554 A1* | 7/2018 | Greene | C10G 3/49 |

* cited by examiner

OLIGOMERIZATION OF ISOBUTANOL IN THE PRESENCE OF MWW ZEOLITE SOLID ACID CATALYSTS

CROSS-REFERENCE TO RELATED APPLICATIONS

This application claims the benefit of priority from U.S. Provisional Application No. 62/967,190 filed Jan. 29, 2020, which is hereby incorporated by reference in its entirety.

FIELD OF THE INVENTION

The present disclosure relates to methods employing a zeolite solid acid catalyst for oligomerizing isobutanol, including bioisobutanol, to form predominantly olefin oligomers larger than $C_8$.

BACKGROUND OF THE INVENTION

The production of ethanol via bioprocessing of biomass may form isobutanol as a main byproduct. In many processes, byproduct isobutanol is produced in sufficient quantities, often in the range of 15%-20% by weight, that it is economically justified to make use of the isobutanol. Thus, methods for processing the isobutanol into jet fuel and other value products have been developed by various industries. Processing the isobutanol into value products usually takes place by two-step conversion technology by first dehydrating the isobutanol to form isobutene, followed by a separate oligomerization reaction of the isobutene. Current conversion technology relies on large-pore microporous zeolites (e.g., Beta, Y, and the like) and amorphous solid acid catalysts to carry out these reactions.

One drawback to using large-pore zeolite catalysts in the foregoing manner is their sensitivity to water, which may be present in the isobutanol feed, but also forms during dehydration. The water can significantly decrease the activity of these zeolite catalysts. Water-induced catalyst deactivation may be mitigated to some extent by increasing the reaction temperature to desorb the water, but high reaction temperatures sufficient to desorb water may instead promote unwanted hydrocarbon cracking and formation of low-value light products. Large-pore zeolite catalysts are also frequently sensitive to impurities, such as fermentation byproducts, typically found in isobutanol feeds derived from bio-ethanol production and may quickly suffer from deactivation when challenged with such feeds.

Another drawback of many conventional zeolite catalysts is their lack of selectivity for producing larger, branched hydrocarbons (e.g., $C_{12}$-$C_{16}$), which may be particularly advantageous for use in producing jet fuels. Without wishing to be bound by theory, it is believed that the pore size and/or pore geometry limits the effective formation of large hydrocarbons when using many conventional zeolites. While small hydrocarbons (e.g., $C_4$ or lower) may easily diffuse into a zeolite pore, large hydrocarbons resulting from oligomerization may find difficulty in leaving a pore. This difficulty effectively blocks the active site of the zeolite catalyst for performing other reactions and simultaneously subjects the hydrocarbon product to conditions which may be favorable for cracking.

SUMMARY OF THE INVENTION

In various embodiments, the present disclosure provides methods comprising: contacting a feed comprising isobutanol with a zeolite solid acid catalyst having a MWW framework under conditions effective to convert the isobutanol into a product comprising $C_{4n}$ olefin oligomers, wherein n is an integer having a value of two or greater and about 80 wt. % or greater of the $C_{4n}$ olefin oligomers are larger than $C_8$.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

DETAILED DESCRIPTION OF THE INVENTION

Figure 1:
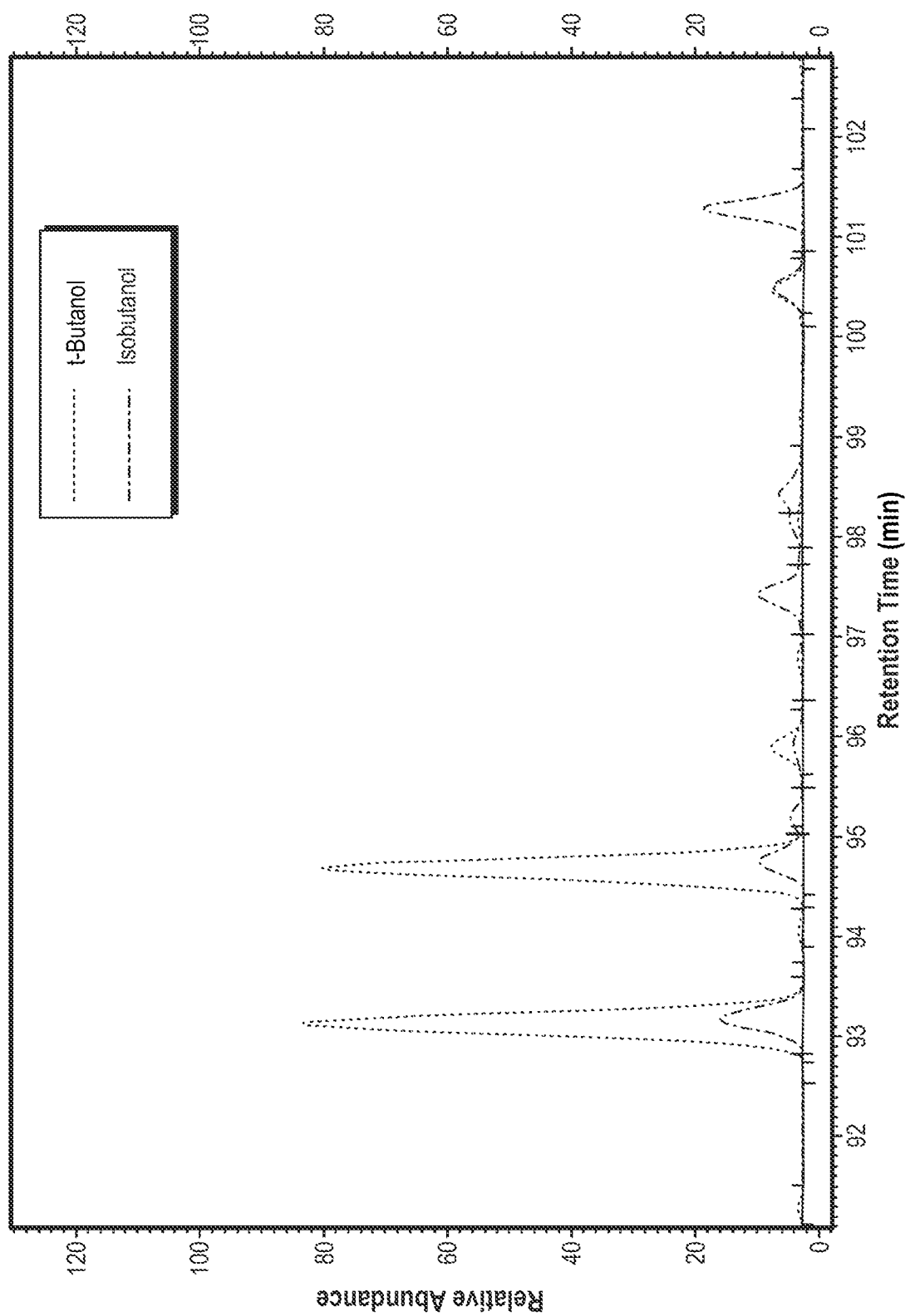
FIG. 1 is a gas chromatograph representative of the $C_8$ fraction of the products derived from the conversion of t-butanol and isobutanol in the absence of co-fed water.

The present disclosure relates to processes for processing isobutanol and, more specifically, processes for oligomerizing isobutanol in the presence of a zeolite solid acid catalyst.

As described further herein, zeolite solid acid catalysts having a MWW framework may convert isobutanol into $C_{4n}$ olefin oligomers directly, rather than through a two-step process of dehydration and oligomerization, as performed with the other processes. In particular, the present disclosure addresses conversion of isobutanol into an olefinic product comprising $C_{4n}$ olefin oligomers, where n is a multiplier and is an integer greater than or equal to 2. Surprisingly, a zeolite solid acid catalyst having a MWW framework may generate a high fraction of $C_{12}$ and $C_{16}$ olefin oligomers from isobutanol in an industrially viable manner, in contrast to the behavior of other feeds and solid acid catalysts.

Advantageously, zeolite solid acid catalysts having a MWW framework, such as MCM-49, exhibit a good balance between acid strength and tolerance toward water, thereby allowing conversion of isobutanol into $C_{4n}$ olefin oligomers to take place at low reaction temperatures, which may lower the incidence of cracking reactions. Moreover, the water tolerance of such zeolite solid acid catalysts allows the dehydration and oligomerization reactions needed to produce $C_{4n}$ olefin oligomers to be coupled together, including conversions taking place within a single reactor, thereby affording further advantages over other zeolite catalysts in which the process steps may be separated from one another. Because the active site geometry of MCM-49 and other MWW framework catalysts is large enough to accommodate $C_{4n}$ olefin oligomers larger than $C_8$, $C_{12}$ and $C_{16}$ oligomers may be formed readily as predominant products, in further contrast to the behavior seen with other zeolite catalysts. While not wishing to be bound by theory, it is believed that much of the conversion activity of zeolite solid acid catalysts having a MWW framework occurs at acid sites in pockets on the exterior surface of the catalyst, which are less prone to active site blockage than are most zeolite catalysts.

Surprisingly, the zeolite solid acid catalysts described herein may convert isobutanol into $C_{4n}$ olefin oligomers with a product distribution significantly different from that obtained when processing t-butanol under similar reaction conditions, even though isobutene may be produced as a putative dehydration intermediate in both instances. Without wishing to be bound by theory, it is hypothesized that dehydration of t-butanol may proceed through a $S_N2$ reaction mechanism, whereas the conversion of isobutanol may take place through a reaction mechanism entirely different from $S_N1$ or $S_N2$. In particular, t-butanol is primarily converted into tribranched Con olefin dimers, with only limited production of higher $C_{4n}$ olefin oligomers, whereas isobutanol predominantly affords larger $C_{4n}$ olefin oligomers, such as $C_{12}$ and $C_{16}$ olefin oligomers conveniently residing in the mid-distillate boiling point range. $C_{12}$ and $C_{16}$ olefin oligomers may be advantageously processed into jet fuel and other value products, rather than having to undergo further reactions in order to increase the carbon count into a more acceptable range. In addition, the $C_8$ olefin oligomers formed from isobutanol are predominantly dibranched, in contrast to the behavior observed with t-butanol.

As mentioned above, most zeolite solid acid catalysts are sensitive to the presence of water, which may lower their catalytic activity. Since water necessarily forms upon dehydration of isobutanol, water deactivation is a considerable problem with other types of zeolite and amorphous acid catalysts. Surprisingly, the catalytic activity of the zeolite solid acid catalysts used herein is not reduced in the presence of water produced during dehydration. Without wishing to be bound by theory, it is believed that water interacts with the active acid sites of MCM-49 and other zeolite solid acid catalysts having a MWW framework to afford active sites having a modified acid strength sufficient to promote further dehydration and subsequent olefin oligomerization in a concerted reaction process.

It has also been surprisingly discovered that the zeolite solid acid catalysts used herein are also not sensitive to small amounts of water intentionally added to the feed ("co-fed water"). For example, the percent conversion of isobutanol in the presence of co-fed water may be reduced by not more than about 5%, by not more than 3%, or by not more than 1% compared to the conversion obtained in the absence of co-fed water. Co-fed water (e.g., up to about 1 cc/hour) may be used to tune the selectivity of the zeolite solid acid catalyst. For example, co-fed water may be used to modulate the ratio between $C_8$ and $C_{12+}$ olefin oligomers, where the fraction of $C_8$ olefin oligomers may increase in the presence of co-fed water.

In addition to their compatibility with water, the zeolite solid acid catalysts employed in the disclosure herein are also compatible with impurities commonly produced during bioethanol production, from which the isobutanol may be conveniently sourced for use in the disclosure herein. For example, an impurity-containing isobutanol feed (e.g., a feed comprising one or more fermentation byproducts) may be continuously conveyed past and contact a zeolite solid acid catalyst having an MWW framework, such as MCM-49, for at least about 1200 hours with little to no loss of catalytic activity, thereby limiting the need for frequent catalyst replacement. In fact, the zeolite solid acid catalysts employed herein may actually convert common bioproduction impurities into valuable products in combination with the $C_{4n}$ olefin oligomers produced from isobutanol. For comparison, large pore microporous zeolite catalysts, such as beta or Y zeolite structures, often exhibit a dramatic drop in catalytic activity after only about 100 hours under similar reaction conditions. Thus, the present disclosure provides advantaged processes for producing highly valued products, such as jet fuel, derivable from renewable biological sources.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise. The term "and/or" as used in a phrase such as "A and/or B" herein is intended to include "A and B," "A or B," "A," and "B." For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds having hydrogen bound to carbon, and encompasses saturated hydrocarbon compounds, unsaturated hydrocarbon compounds, and mixtures of hydrocarbon compounds (saturated and/or unsaturated), including mixtures of hydrocarbon compounds having different numbers of carbon atoms.

The term "$C_n$" refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic. Similarly, the term "$C_{n-}$" refers to a hydrocarbon(s) or a hydrocarbyl group having n or fewer carbon atom(s) per molecule or group, and the term "$C_{n+}$" refers to a hydrocarbon(s) or hydrocarbyl group having n or greater carbon atom(s) per molecule or group.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The term "branched" refers to a hydrocarbon having a linear carbon chain or a closed carbon ring, in which a hydrocarbyl side chain extends from the linear carbon chain or the closed carbon ring. The term "linear" refers to a hydrocarbon or hydrocarbyl group having a continuous carbon chain without side chain branching, in which the continuous carbon chain may be optionally substituted with heteroatoms or heteroatom groups.

The term "oligomer" refers to a molecule having a predetermined number of repeating monomer units, where the number of repeating monomer units is relatively small and specifiable. Illustrative oligomers include dimers, trimers, tetramers, higher oligomers, and mixtures thereof. For purposes of this disclosure, when an oligomer is referred to as comprising an olefin, such as isobutylene, the olefin is present in the oligomer in an oligomerized form.

According to the present disclosure, methods for generating C$_{4n}$ olefin oligomers from isobutanol may comprise contacting a feed comprising isobutanol with a zeolite solid acid catalyst having a MWW framework under conditions effective to convert the isobutanol into a product comprising C$_{4n}$ olefin oligomers, wherein n is an integer having a value of 2 or greater and about 80 wt. % or greater of the C$_{4n}$ olefin oligomers are larger than C$_8$ (i.e., C$_8$+). As used herein, the term "C$_{4n}$ olefin oligomer" refers to an oligomer putatively formed from isobutene and bearing at least one carbon-carbon double bond.

The term "zeolite" refers to a crystalline material having a porous framework structure built from tetrahedral atoms connected by bridging oxygen atoms, a large number of which are known to persons having ordinary skill in the art. Under this definition, the term "zeolite" may refer to aluminosilicates having a zeolitic framework type as well as crystalline structures containing oxides of heteroatoms different from silicon and aluminum. Such heteroatoms may include any heteroatom generally known to be suitable for inclusion in a zeolitic framework, such as gallium, boron, germanium, phosphorus, zinc, antimony, tin, and/or other transition metals that can substitute for silicon and/or aluminum in a zeolitic framework. Any of the catalysts disclosed herein as being suitable for use in forming C$_{4n}$ olefin oligomers may include such heteroatom substitution in particular instances.

As used herein, zeolites having a MWW framework may include one or more of: a) molecular sieves made from a common first-degree crystalline building block unit cell, where the unit cell has the MWW framework topology; b) molecular sieves made from a common second-degree building block with a 2-dimensional tiling of such MWW framework topology unit cells, forming a monolayer of one unit cell thickness, preferably one c-unit cell thickness; and c) molecular sieves made from common second-degree building blocks, with layers of one or more than one unit cell thickness, wherein the layer of more than one unit cell thickness is made from stacking, packing, or binding at least two monolayers of MWW framework topology unit cells. The stacking of such second-degree building blocks can be in a regular fashion, an irregular fashion, a random fashion, or any combination thereof. Molecular sieves made by any regular or random 2-dimensional or 3-dimensional combination of unit cells having a MWW framework may also be made.

Crystalline zeolite solid acid catalysts having a MWW framework may include molecular sieves having an X-ray powder diffraction pattern including d-spacing maxima at 12.4±0.25, 6.9±0.15, 3.57±0.07 and 3.42±0.07 Å. The X-ray powder diffraction data used for such characterization may be obtained by standard techniques using the K-alpha doublet of copper as incident radiation and a diffractometer equipped with a scintillation counter and an associated computer as the collection system.

Zeolite solid acid catalysts having a MWW framework suitable for use in the present disclosure may include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof. MCM-49 may be a particularly suitable zeolite solid acid catalyst for use in the disclosure herein. Suitable zeolite solid acid catalysts for use in the disclosure herein may include aluminosilicate materials having a silica to alumina molar ratio of at least about 10, such as at least about 10 to about 50 or less. One or more heteroatoms may be present in a zeolite solid acid catalyst, as referenced above. In addition, zeolite solid acid catalysts may be may be contaminated with other crystalline materials, such as ferrierite or quartz. These contaminants may be present in quantities of less than about 10 wt. %, normally less than about 5 wt. %.

A zeolite solid acid catalyst may be optionally combined with a binder when used in the methods and systems disclosed herein. Such binders may include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with oxide-type binders to modify the mechanical properties of the catalyst or to assist in its manufacture. The relative proportions of zeolite and binder may vary widely. For example, the amount of binder employed, if employed, may be as little as about 0.01 wt. %, or at least about 1 wt. %, or at least about 5 wt. %, or at least about 10 wt. %, or up to about 90 wt. %, or up to about 80 wt. %, or up to about 70 wt. %, or up to about 60 wt. %, or up to about 50 wt. % binder.

Optionally, ion exchange may be performed upon a bound zeolite solid acid catalyst such as with ammonium nitrate, for example.

Isobutanol may be converted into $C_{4n}$ olefin oligomers under a range of effective reaction conditions. Effective reaction conditions may be described in terms of pressure, temperature, feed rate, and/or liquid hourly space velocity (LHSV). For example, a reaction vessel housing a zeolite solid acid catalyst may be operated at a temperature of about 100° C. to about 300° C. Additionally or alternatively, a reaction vessel may be operated at a pressure of about atmospheric pressure (~15 psig, ~103 KPa) up to about 1000 psig (6.894 MPa). Additionally or alternatively, a reaction vessel may be operated at a LHSV of about 0.25 hour$^{-1}$ to about 6 hour$^{-1}$. Additionally or alternatively, hydrogen may be co-fed with isobutanol at an $H_2$:isobutanol molar ratio of about 0.1 to about 10.

As mentioned previously, zeolite solid acid catalysts having a MWW framework may convert isobutanol directly into one or more $C_{4n}$ olefin oligomers, particularly in a single reactor or vessel. In a particular example, the isobutanol may be contacted with the zeolite solid acid catalyst at or near the top of the reactor vessel, and the $C_{4n}$ olefin oligomers may be obtained from the bottom of the reactor vessel. The zeolite solid acid catalyst may be arranged in a fixed bed configuration when contacting the isobutanol in this manner, such that the isobutanol and the $C_{4n}$ olefin oligomers progress in a trickle bed fashion through the reactor. Unconverted isobutanol obtained from the reactor may be separated from the $C_{4n}$ olefin oligomers and recycled to the isobutanol feed supplying the reactor. Alternately, other reactor configurations such as batch, fluidized bed, and/or slurry reactors may be used when forming $C_{4n}$ olefin oligomers according to the disclosure herein.

Suitable feeds comprising isobutanol may be obtained from any source for use in the present disclosure. In particularly advantageous process configurations, the isobutanol may be biologically derived, such as through formation as a byproduct of producing bioethanol through fermentation. Feeds derived from such fermentation sources may additionally comprise impurities including members such as, but not limited to, water, ethanol, xylose, furfural, lactic acid, 5-hydroxymethylfurfural (HMF), and any combination thereof. Water and/or organic fermentation impurities may be removed from an isobutanol feed prior to processing according to the disclosure herein, but preferably may remain with the isobutanol while undergoing conversion according to the disclosure herein in order to maintain process simplicity. Suitable feedstocks for producing isobutanol through fermentation will be familiar to one having ordinary skill in the art and are not believed to be particularly limited.

The products generated according to the present disclosure may comprise a high weight percentage of branched $C_{4n}$ olefin oligomers. In particular, a product formed in accordance with the present disclosure may comprise a blend of $C_{4n}$ olefin oligomers and isomeric forms thereof having a wide range of numbers of branches, different branch locations, lengths, and further substitution. A blend of $C_{4n}$ olefin oligomers may have one or more double bonds varying in locations and total number per molecule. Branching in a product as a whole may be characterized by the branch index. A product obtained according to the present disclosure may have a branch index of 1 or greater, indicating that a majority of the $C_{4n}$ olefin oligomers have at least one branch. Any given $C_{4n}$ olefin oligomer in a product may be mono-branched, dibranched, tribranched or have four or greater branches. In a particular example, at least about 90 wt. % of $C_{4n}$ olefin oligomers may have at least one branch.

Branch Index within a mixture of branched olefin oligomers equals (0×% linear olefins+1×% monobranched olefins+2×% dibranched olefins+3×% tribranched olefins)/100; where % linear olefins+% monobranched olefins+% dibranched olefins+% tribranched olefins=100%. More highly branched individual olefins (e.g., tetrabranched and higher) may be weighted similarly to determine the branch index. For example, a mixture of $C_8$ olefin oligomers composed of 10% linear $C_8$, 30% monobranched $C_8$, 50% dibranched $C_8$, and 10% tribranched $C_8$ has a branch index of 1.6.

Isobutanol may be converted to a product comprising a high percentage of $C_{4n}$ olefin oligomers, wherein a substantial majority of the $C_{4n}$ olefin oligomers are larger than $C_8$. Conversion of the isobutanol into $C_{4n}$ olefin oligomers and any other products may range from about 40% to about 100% of the isobutanol by weight, depending on reaction conditions. For example, in the absence of co-fed water, isobutanol may be converted to a product comprising about 80 or 90 wt. % or greater of $C_{4n}$ olefin oligomers larger than $C_8$. In particular examples produced in the absence of co-fed water, a product may comprise at least about 45 wt. % $C_{12}$ olefin oligomers and/or at least about 30 wt. % $C_{16}$ olefin oligomers. For example, a feed comprising isobutanol may be converted into a product comprising about 70 wt. % or greater, or about 80 wt. % or greater, or about 90 wt. % or greater of $C_{12}$ and $C_{16}$ olefin oligomers (i.e., $C_{4n}$ olefin oligomers where n is 3 or 4). In the absence of co-fed water, a product may comprise a minor fraction of $C_8$ olefin oligomers formed from isobutanol. For example, a product derived from a feed comprising isobutanol but without intentionally added or introduced water may comprise about 30 wt. % or less, or about 20 wt. % or less, or about 10 wt. % or less (i.e., 0 wt. % to about 10 wt. %) of $C_8$ olefin oligomers. Those $C_8$ olefin oligomers that do form may include predominant dibranching, in contrast to the behavior exhibited by t-butanol, which forms predominantly tribranched $C_{4n}$ olefin oligomers. In a particular example, at least about 80 wt. % of the $C_8$ olefin oligomers may be dibranched.

Advantageously, the selectivity for $C_8$ versus $C_{9+}$ olefin oligomers may be altered based on the presence of co-fed water. In the presence of co-fed water, isobutanol may be converted to a product comprising $C_{4n}$ olefin oligomers, wherein a substantial majority of the $C_{4n}$ olefin oligomers is $C_8$. Suitable amounts of co-fed water may include an effective amount for maintaining catalytic activity, such as about 1 cc/hr or less, for example. The co-fed water may be present with the isobutanol or be provided as a separate feed. By co-feeding water in a suitable amount, isobutanol may be converted to a product comprising about 70 wt. % or greater of $C_8$ olefin oligomers, about 80 wt. % or greater of $C_8$ olefin oligomers, or about 90 wt. % or greater of $C_8$ olefin oligomers. The balance of the product may comprise unconverted isobutanol or $C_{9+}$ olefin oligomers. For example, a product derived from a feed wherein water is co-fed with the feed may comprise about 30 wt. % or less, or about 20 wt. % or less, or about 10 wt. % or less (i.e., 0 wt. % to about 10 wt. %) of $C_{9+}$ olefin oligomers.

The zeolite solid acid catalysts having an MWW framework used in the present disclosure may exhibit low cracking activity. Thus, any product formed in accordance with the disclosure herein may comprise a low percentage of $C_{3-}$ hydrocarbons. In a particular example, less than about 0.01 wt. % of the isobutanol may be converted into $C_{3-}$ hydrocarbons. Preferably, a product formed in accordance with the present disclosure may contain no $C_{3-}$ hydrocarbons in combination with the $C_{4n}$ olefin oligomers. In other particular examples, a product formed in accordance with the present disclosure may comprise less than about 0.01 wt. % (i.e., from 0 wt. % to about 0.01 wt. %) $C_{3-}$ hydrocarbons based on the total weight of the product.

Since water is produced in the course of dehydrating isobutanol, products formed in accordance with the disclosure herein may comprise at least some water. Water may be separated from the $C_{4n}$ olefin oligomers, such as through drying or distillation, if needed to facilitate further use thereof.

After formation, a product of the present disclosure may be conveyed through a product outlet to a separation stage. Various fractions of the product may be separated from each other in the separation stage and/or water may be removed from the product or a fraction thereof. Unconverted isobutanol remaining in a product may be separated and recycled to the feed, if desired, entering at the top of the reactor vessel. The remaining hydrocarbons may be subjected to further processes to isolate desired fractions, such as $C_8$ olefin oligomers or $C_{12+}$ olefin oligomers. In a particular example, dimethylhexane may be isolated as a valuable fraction from a product following hydrogenation. Isolated fractions of a product may be conveyed to further downstream processes, if necessary, to generate commercially valuable isoparaffin products such as solvents (e.g., ISOPAR™, available from Exxon Mobil Co., Houston, Tex., USA), jet fuel, and the like.

Optionally, a product or a given fraction thereof may be further hydrogenated to form a reduced product comprising $C_{4n}$ paraffins or isoparaffins, wherein n is defined as above. Hydrogenation may be carried out by contacting one or more of the $C_{4n}$ olefin oligomers in the product with a hydrogenation catalyst and hydrogen under conditions effective to reduce the olefins in a product to the corresponding paraffins or isoparaffins. Suitable hydrogenation catalysts for hydrogenating the $C_{4n}$ olefin oligomers to form $C_{4n}$ paraffins or isoparaffins may include, for example, an insoluble metal such as palladium (Pd/C), platinum (PtO$_2$), or nickel (Raney-Nickel). In a more specific example, formation of the $C_{4n}$ olefin oligomers and hydrogenation of the $C_{4n}$ olefin oligomers may take place in a single reactor, where hydrogen is co-fed with an isobutanol feed, which is then contacted with the zeolite solid acid catalyst in an upstream portion of the reactor. The resulting $C_{4n}$ olefin oligomers may then travel downstream, where they may be contacted with a hydrogenation catalyst in the downstream portion of the single reactor, effectively converting the $C_{4n}$ olefin oligomers to $C_{4n}$ paraffins or isoparaffins. The two catalysts may be in separate beds in such process configurations. Optionally, the two catalysts may be in separate beds spaced apart from one another by an inert material through which the $C_{4n}$ olefin oligomers pass sequentially in the course of forming $C_{4n}$ paraffins or isoparaffins. In another alternative process configuration, the two catalysts may be stacked on top of one another without an inert material in between.

Embodiments Disclosed Herein Include

A. Methods for processing isobutanol into oligomers. The methods comprise: contacting a feed comprising isobutanol with a zeolite solid acid catalyst having a MWW framework under conditions effective to convert the isobutanol into a product comprising $C_{4n}$ olefin oligomers, wherein n is an integer having a value of two or greater and about 80 wt. % or greater of the $C_{4n}$ olefin oligomers are larger than $C_8$.

Embodiment A may have one or more of the following elements in any combination:

Element 1: wherein about 90 wt. % of the $C_{4n}$ olefin oligomers are larger than $C_8$.

Element 2: wherein the zeolite solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and any combination thereof.

Element 3: wherein the zeolite solid acid catalyst is MCM-49.

Element 4: wherein the isobutanol is biologically derived.

Element 5: wherein the isobutanol is formed as a byproduct of producing bioethanol.

Element 6: wherein the feed further comprises one or more fermentation byproducts.

Element 7: wherein the one or more fermentation byproducts comprise at least one member selected from the group consisting of ethanol, xylose, furfural, lactic acid, 5-hydroxymethylfurfural, and any combination thereof.

Element 8: wherein the contacting is performed in an absence of co-fed water.

Element 9: wherein the product comprises at least about 45 wt. % $C_{12}$ olefin oligomers.

Element 10: wherein the product comprises at least about 30 wt. % $C_{16}$ olefin oligomers.

Element 11: wherein the product comprises $C_8$ olefin oligomers and at least about 80 wt. % of the $C_8$ olefin oligomers are dibranched.

Element 12: wherein less than about 0.1 wt. % of the isobutanol is converted into $C_{3-}$ hydrocarbons.

Element 13: wherein the method further comprises: hydrogenating the $C_{4n}$ olefin oligomers to form $C_{4n}$ isoparaffins.

Element 14: wherein formation of the $C_{4n}$ olefin oligomers and hydrogenation of the $C_{4n}$ olefin oligomers take place in a single reactor, the feed being contacted with the zeolite solid acid catalyst in an upstream portion of the single reactor and the $C_{4n}$ olefin oligomers being contacted with a hydrogenation catalyst in a downstream portion of the single reactor.

Element 15: wherein the formation of the $C_{4n}$ olefin oligomers and hydrogenation of the $C_{4n}$ olefin oligomers take place in separate reactors.

Element 16: wherein the method further comprises recycling unconverted isobutanol to the feed.

Element 17: wherein the conditions effective to convert the isobutanol comprise one or more of a temperature of about 100° C. to about 300° C., a pressure ranging from atmospheric pressure up to about 1000 psig, and an liquid hourly space velocity (LHSV) of about 0.25 hour$^{-1}$ to about 6 hour$^{-1}$.

Element 18: wherein contacting takes place in a fixed catalyst bed reactor, a batch reactor, a slurry reactor, or a fluidized bed reactor.

Element 19: wherein the method further comprises: processing the $C_{4n}$ olefin oligomers into a jet fuel.

Illustrative combinations applicable to A include, but are not limited to: 1 and 2; 1 and 3; 1 and 4; 1 and 5; 1 and 6; 1 and 8; 1 and 11; 1 and 13; 1, 13 and 14; 1 and 17; 2 or 3 and 4; 2 or 3 and 5; 2 or 3 and 6; 2 or 3, 6 and 7; 2 or 3 and 8; 2 or 3, 8 and 9; 2 or 3, 8 and 10; 2 or 3 and 8-10; 2 or 3 and 11; 2 or 3 and 13; 2 or 13 and 17; 8 and 9; 8 and 10; 8-10; 8, 9 and 13; 8, 10 and 13; 8-10 and 13; 8, 9 and 17; 8, 10 and 17; and 8-10 and 17.

To facilitate a better understanding of the embodiments of the present invention, the following examples of preferred or representative embodiments are given. In no way should the following examples be read to limit, or to define, the scope of the invention.

EXAMPLES

Catalyst Synthesis

MCM-49 zeolite crystals (80 wt. % on a dry calcined basis) were combined with pseudoboehmite alumina (20 wt. % on a dry calcined basis) in a mixer and mixed for about 10 minutes to about 30 minutes. Water and polyvinyl alcohol (0.05 wt. %) were added to the mixture to produce an extrudable paste, which was formed into a 0.05-inch (0.127 cm) quadrulobe extrudate using an extruder. After extrusion, the extrudate was dried at a temperature of about 250° F. (121° C.) to about 325° F. (168° C.). After drying, the extrudate was heated to about 1000° F. (538° C.) under flowing nitrogen. The extrudate was then cooled to ambient temperature and humidified with saturated air or steam.

After humidification, the extrudate was ion-exchanged with aqueous ammonium nitrate (about 0.5N to about 1 N). The ion-exchange was performed twice. The exchanged extrudate was then washed with deionized water to remove residual nitrate. After washing, the extrudate was dried and then calcined in nitrogen/air at a temperature of about 1000° F. (538° C.).

Reactor.

A stainless steel tube having dimensions of 0.375 inches (0.95 cm) diameter by 20.5 inches (52.07 cm) long by 0.035 inches (0.09 cm) wall thickness was used as a reactor. A piece of stainless steel tubing having dimensions of 0.375 inches (0.95 cm) outer diameter by 8.75 inches (22.23 cm) long and a piece of 0.25 inch (0.635 cm) tubing of similar length was used in the bottom of the reactor as a spacer (one nested inside of the other) to position and support the catalyst in the isothermal zone of the furnace. A plug of glass wool (0.25 inch (0.635 cm)) was placed at the top of the spacer to keep the catalyst in place. A stainless steel thermowell (0.16 inch (0.40 cm)) sufficiently long to monitor temperature throughout the catalyst bed using a movable thermocouple was placed in the catalyst bed.

MCM-49 zeolite was extruded with alumina binder at a ratio of 80 wt. % catalyst to 20 wt. % alumina as described above, resulting in a solid acid MCM-49 zeolite catalyst sized about 14 mesh (~1.41 mm) to about 25 mesh (~0.707 mm). The solid acid MCM-49 zeolite catalyst (about 4.0 g) was loaded into the reactor through the top of the reactor to create a fixed catalyst bed about 10 cm to about 12.5 cm in depth. A 0.25-inch (0.635 cm) plug of glass wool was placed on top of the catalyst bed to separate the catalyst from quartz chips, which were used to fill the remaining void at the top of the reactor. The reactor was installed in a furnace such that the catalyst bed was located roughly at the center of the furnace at a pre-marked isothermal zone. The reactor was pressure and leak tested at 800 psig (5.5 MPa). The reactor was equipped with a backpressure controller (Mity Mike, available from Grove) to control reactor pressure.

Alcohol feed was introduced into the reactor using two 500 mL ISCO syringe pumps. The reactor was operated at a pressure of 750 psig (5.17 MPa). Online gas chromatography (GC) analyses were performed to verify feed and product composition. Feed was conveyed through the catalyst bed held at a fixed temperature. Product exiting the reactor flowed through heated lines routed to an online GC sampling location and then to a chilled collection vessel to condense the product. The non-condensable gas products exiting the chilled collection vessel were routed through a gas pump for GC analysis. Samples from the collection vessels were also taken for analysis. Every 24 hours, the GC data obtained from collection vessel samples and gas pump analyses were compared against the GC data of the reactor effluent to check material balances.

Example 1. Conversion of t-Butanol and Isobutanol with MCM-49

Figure 2:
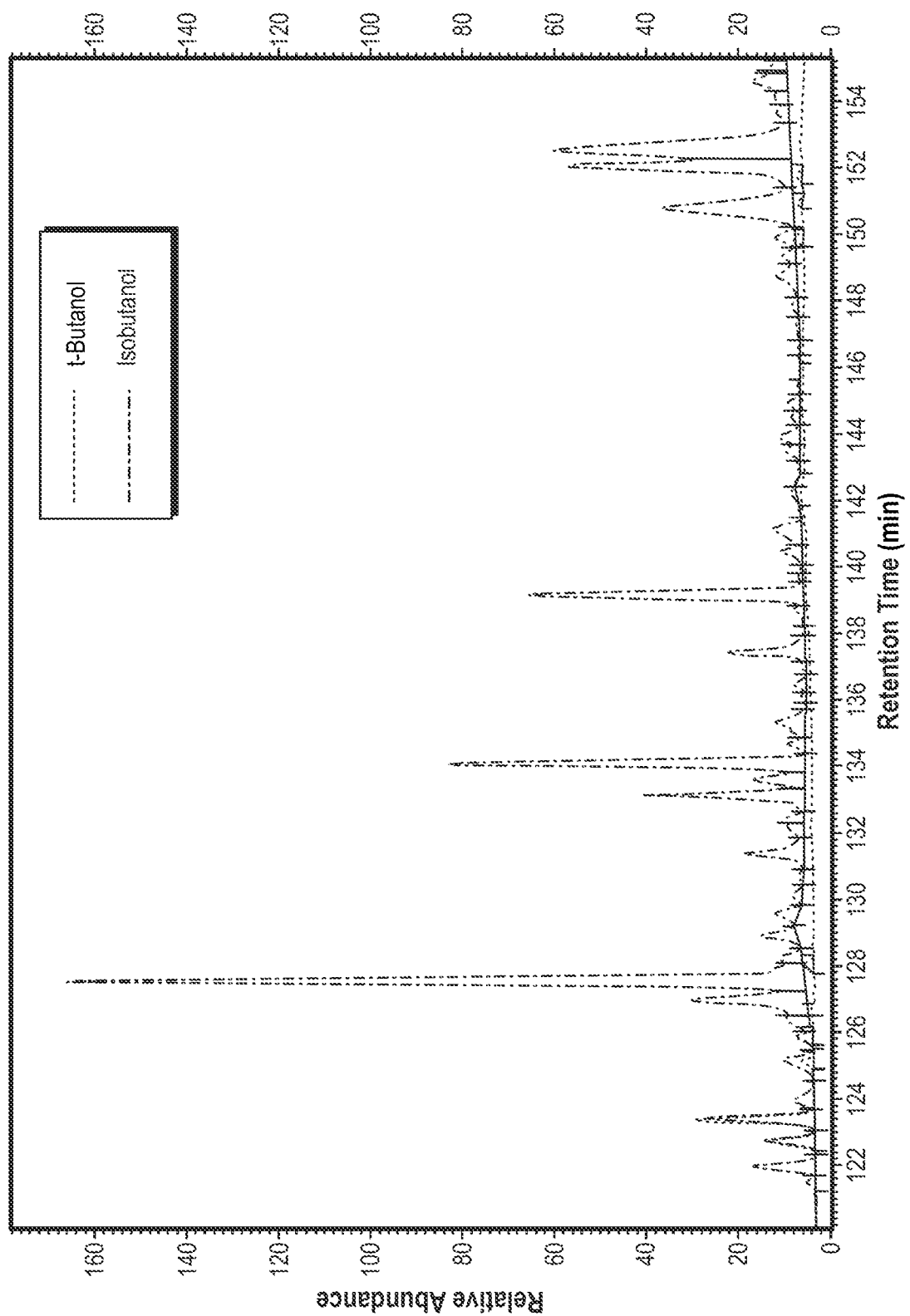
FIG. 2 is a gas chromatograph representative of the $C_{12}$ fraction of the products derived from the conversion of t-butanol and isobutanol in the absence of co-fed water.

Isobutanol was introduced into the reactor as feed. For a comparative example, t-butanol was also introduced separately into the reactor under similar reaction conditions. Each conversion reaction was conducted over a period of a few days at a temperature of about 180° C., an initial LHSV of about 0.5 hour$^{-1}$, and a pressure of 750 psig (5.17 MPa). The GC analyses of the product streams revealed that MCM-49 was an active, stable catalyst for converting both t-butanol and isobutanol to olefin products. However, the compositions of the products obtained were completely different, each exhibiting a different distribution of individual reaction products. Example data collected from GC analyses of the product of each of the reactions is shown in FIGS. 1 and 2 for isobutanol and t-butanol, respectively. Isobutene afforded still another distinct product composition under similar reaction conditions, as shown by GC analyses (FIG. 3) and discussed further below (Example 2).

Figure 4:
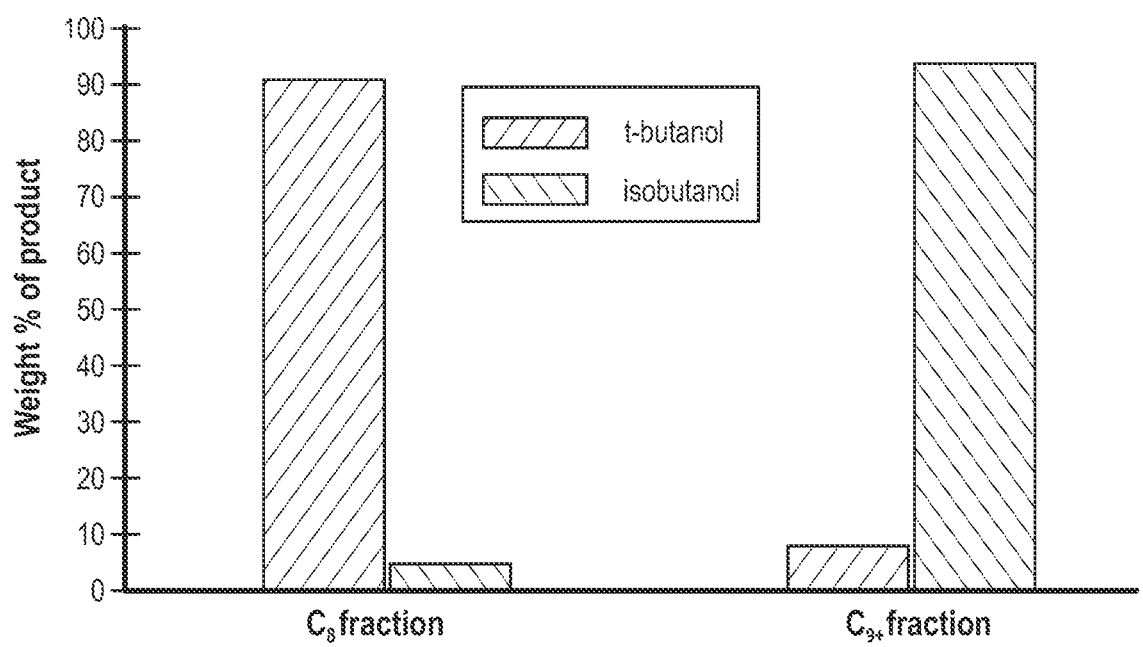
FIG. 4 is a bar graph showing the relative weight percentages of $C_8$ and $C_{9+}$ olefin oligomers in a product derived from isobutanol as compared to a product derived from t-butanol.
Figure 5:
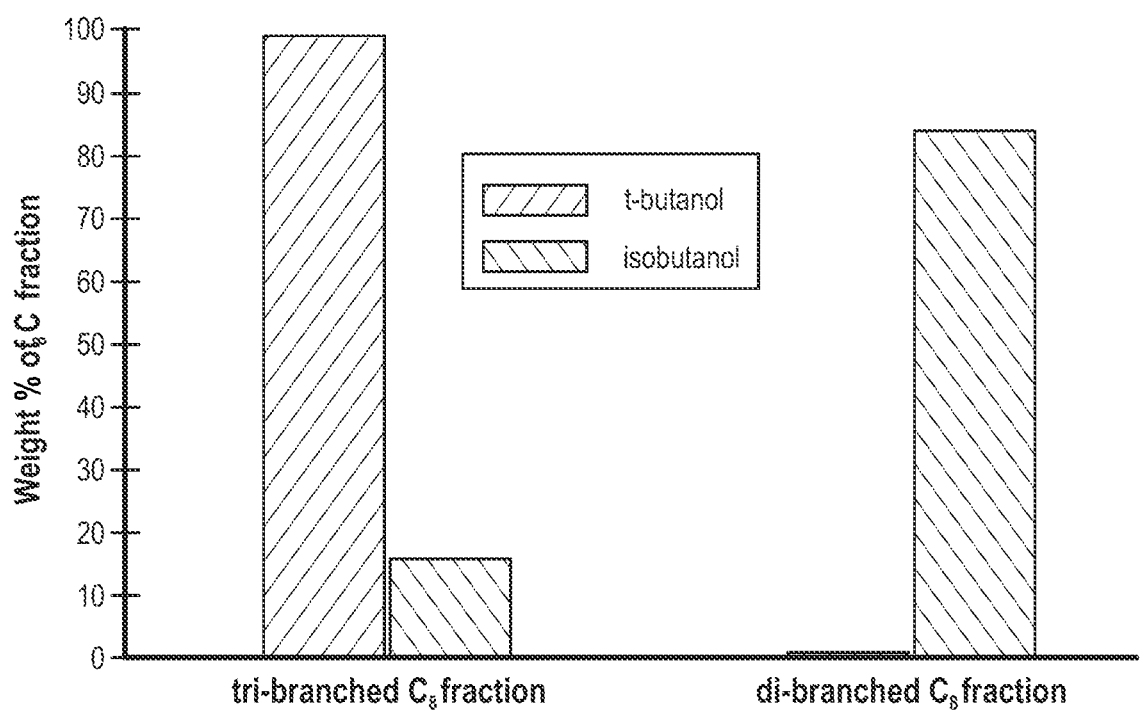
FIG. 5 is a bar graph showing the relative weight percentages of tribranched $C_8$ olefin oligomers and dibranched $C_8$ olefin oligomers derived from isobutanol as compared to those derived from t-butanol.
Figure 9:
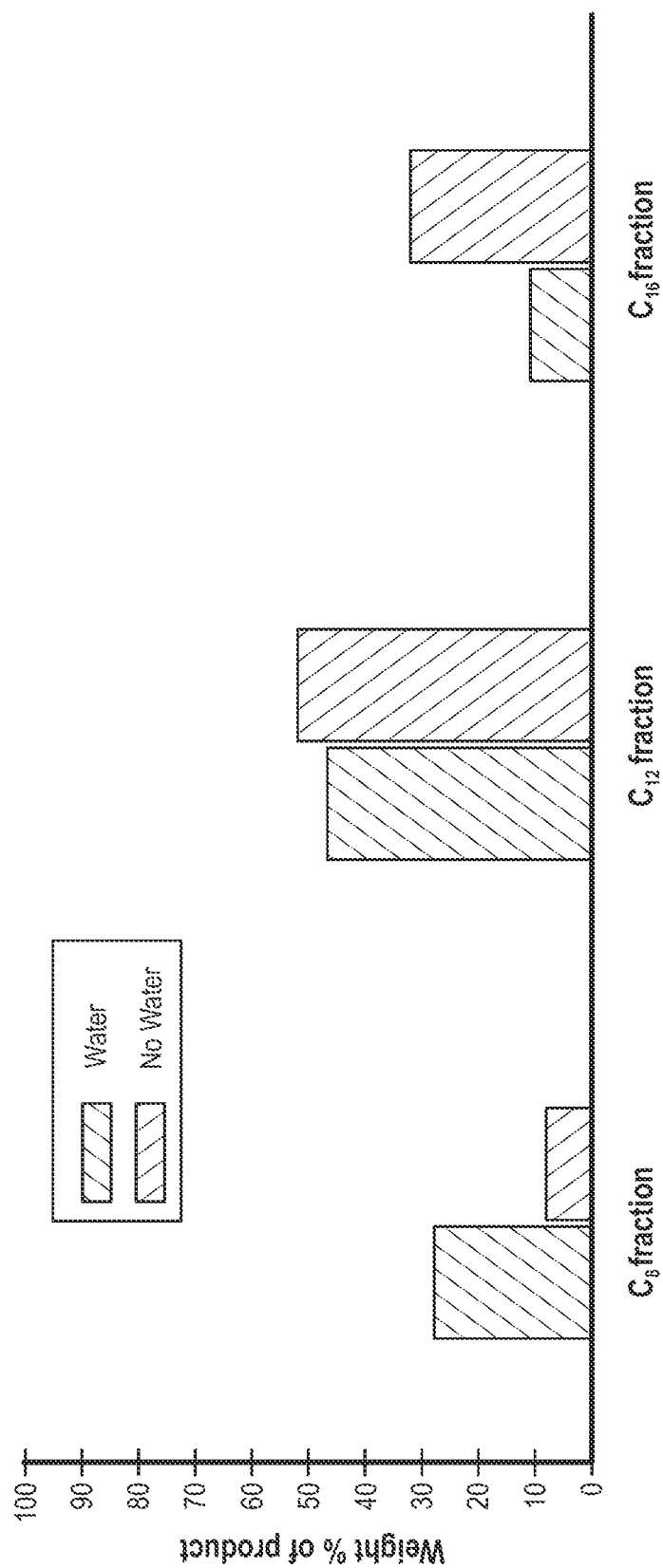
FIG. 9 is a bar graph showing the effect of co-fed water on the relative percentages of $C_8$, $C_{12}$, and $C_{16}$ olefin oligomers in a product generated from the conversion of isobutanol by a zeolite solid acid catalyst having a MWW framework.

Notably, the conversion of a feed comprising t-butanol resulted in a higher fraction of $C_8$ olefin oligomers in comparison to the performance observed with isobutanol, which afforded a higher fraction of $C_{12}$ olefin oligomers and a significant fraction of $C_{16}$ olefin oligomers. The percentages of $C_8$ olefin oligomers and $C_{9+}$ olefin oligomers in the product were calculated for each feed. The results are shown in the bar graph of FIG. 4. Additionally, the branching of the $C_8$ olefin oligomers generated from t-butanol versus isobutanol were different. FIG. 5 shows a bar graph illustrating the distribution of tribranched $C_8$ olefin oligomers and dibranched $C_8$ olefin oligomers in products generated from each feed. Compared to t-butanol, isobutanol was converted to more dibranched $C_8$ olefin oligomers, which may be a particularly valuable fraction to isolate for chemical applications (e.g., dimethylhexane). The $C_8$ olefins analyzed in FIG. 5 were formed in the absence of co-fed water. FIG. 9 shows a bar graph depicting additional data directed to the relative amounts of $C_8$, $C_{12}$, and $C_{16}$ olefin oligomers generated from isobutanol in the presence of and in the absence of added water.

Example 2. Effect of Water on Conversion of Isobutene with MCM-49

Figure 3:
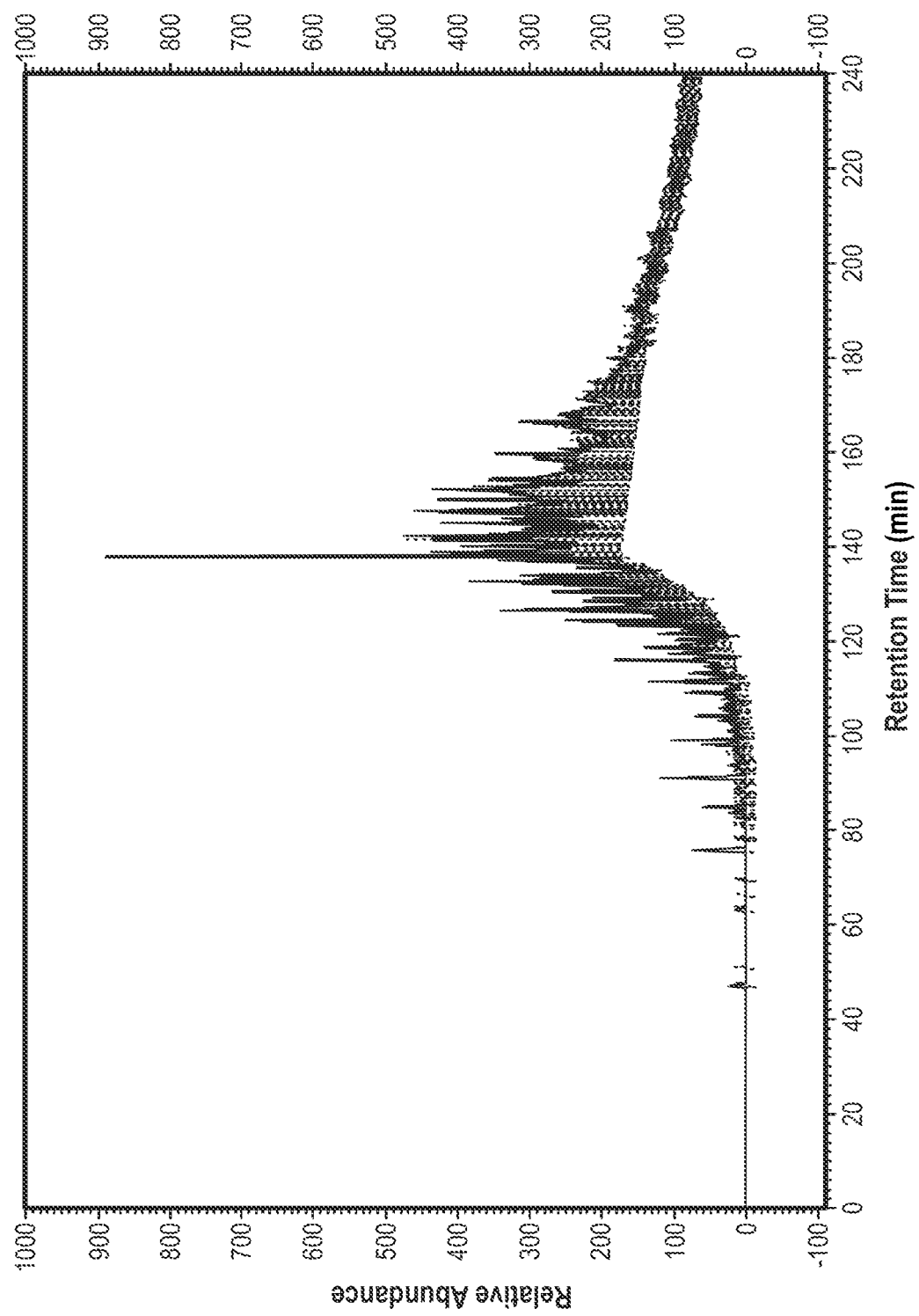
FIG. 3 is a gas chromatograph representative of the products derived from the conversion of isobutene in the absence of co-fed water.
Figure 6:
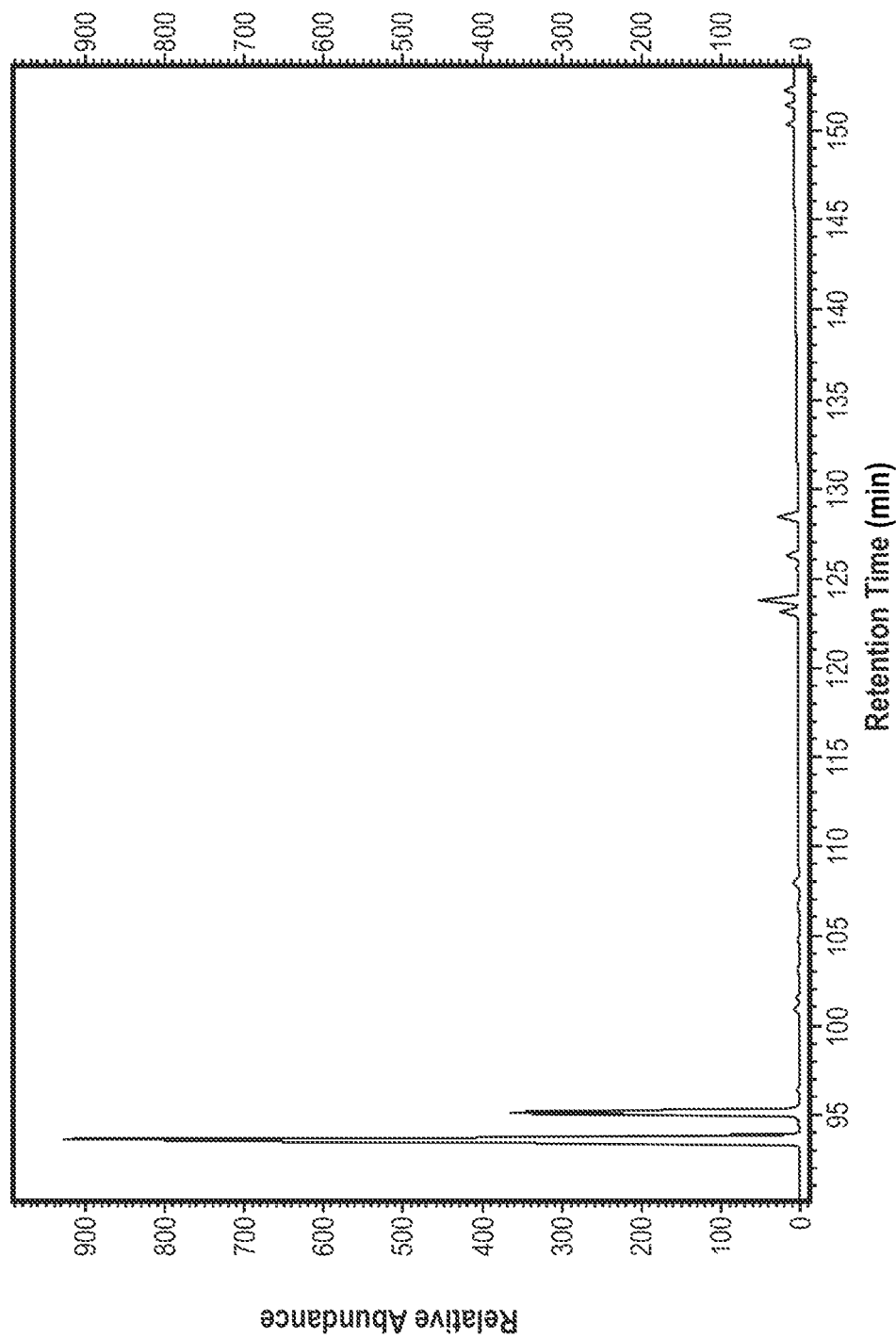
FIG. 6 is a gas chromatograph representative of the products derived from the conversion of isobutene in the presence of co-fed water by a zeolite solid acid catalyst having a MWW framework.
Figure 7:
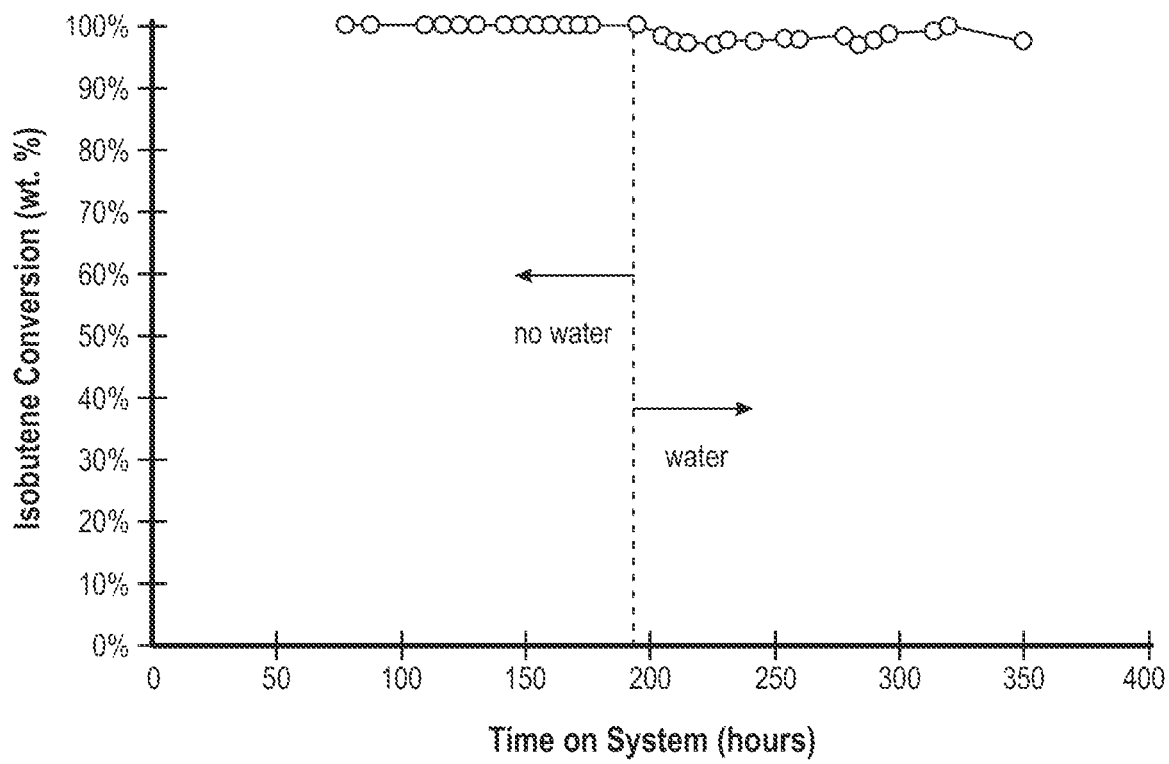
FIG. 7 is a graph showing the effect of co-fed water on the conversion of isobutene by a zeolite solid acid catalyst having a MWW framework.
Figure 8:
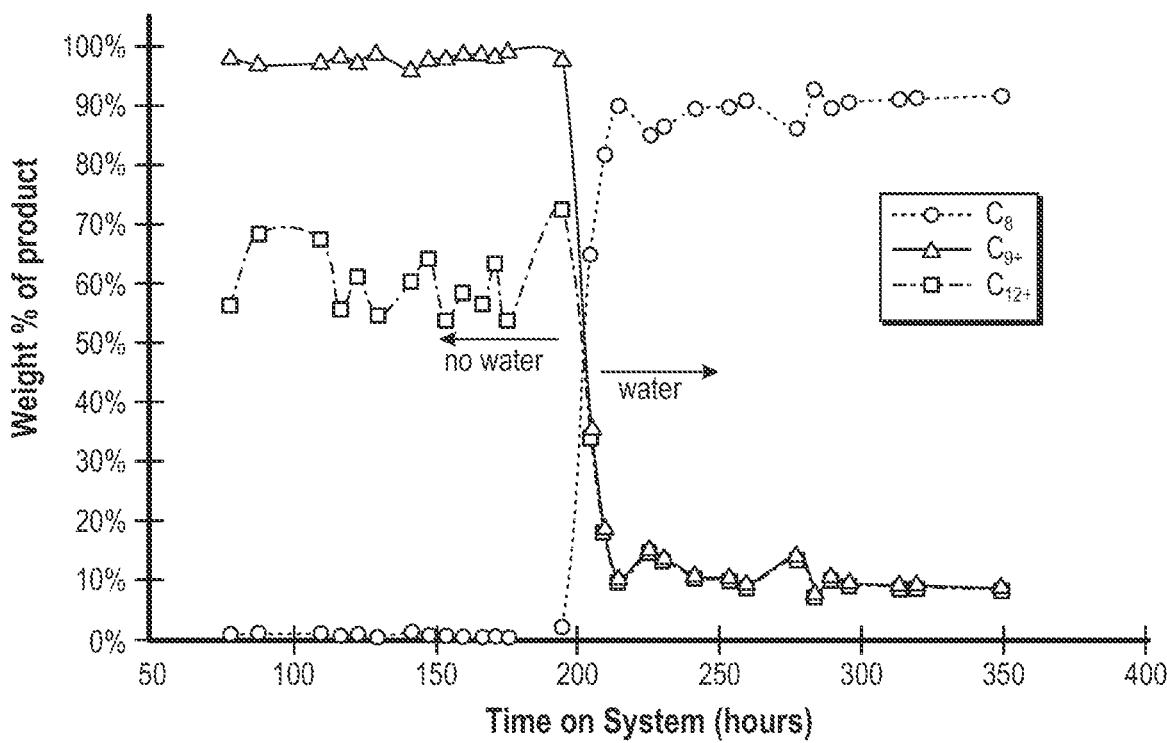
FIG. 8 is a graph showing the effect of co-fed water on the relative percentages of $C_8$, $C_{9+}$, and $C_{12+}$ olefin oligomers in a product generated from the conversion of isobutene by a zeolite solid acid catalyst having a MWW framework.

Conversion was carried out as described in Example 1 using isobutene or isobutene/water as the feed. The reaction was conducted over a period of a few days at a temperature of about 180° C., an initial LHSV of about 0.5 hour$^{-1}$, and a pressure of 750 psig (5.17 MPa). When included, 0.78 cc/hour water was co-fed with the isobutene. FIG. 6 shows example data collected from GC analysis of the product formed from the conversion of isobutene in the presence of co-fed water. FIG. 3 shows the corresponding GC analysis in the absence of co-fed water. As shown, the product distributions were significantly different depending on whether co-fed water was present, but the co-fed water did not substantially impact conversion of the feed on the whole, as shown in FIG. 7, which demonstrates that co-fed water did not substantially change the conversion of feed to $C_{4n}$ olefin oligomers over about 200 hours of contacting time. However, as shown in FIG. 8, water may alter the product distribution, specifically the relative amounts of $C_8$ and $C_{9+}$ olefin oligomers formed in the product. Notably, in the presence of co-fed water, the selectivity for forming $C_8$ olefin oligomers increased drastically over forming larger oligomers. While not wishing to be bound by theory, it is believed that the presence of water affects product formation by delocalizing the positive charge and decreasing acid strength of the catalyst. Notably, the product distribution starting from an isobutene or isobutene/water feed afforded a significantly different product distribution than did isobutanol or isobutanol/water.

Example 3. Conversion of Isobutanol in Comparison to Bioisobutanol

Conversion reactions were performed as described in Example 1. The feed was isobutanol or isobutanol having the impurities as shown below in Table 1 below, which are representative of certain impurities found in bioisobutanol derived from the fermentation of biomass.

TABLE 1

| | |
|---|---|
| Ethanol | 4.0 ppm |
| Xylose | 0.5 ppb |
| HMF | 23.4 ppm |
| Furfural | 7319.9 ppm |
| Lactic acid | 14.1 ppm |

Figure 10:
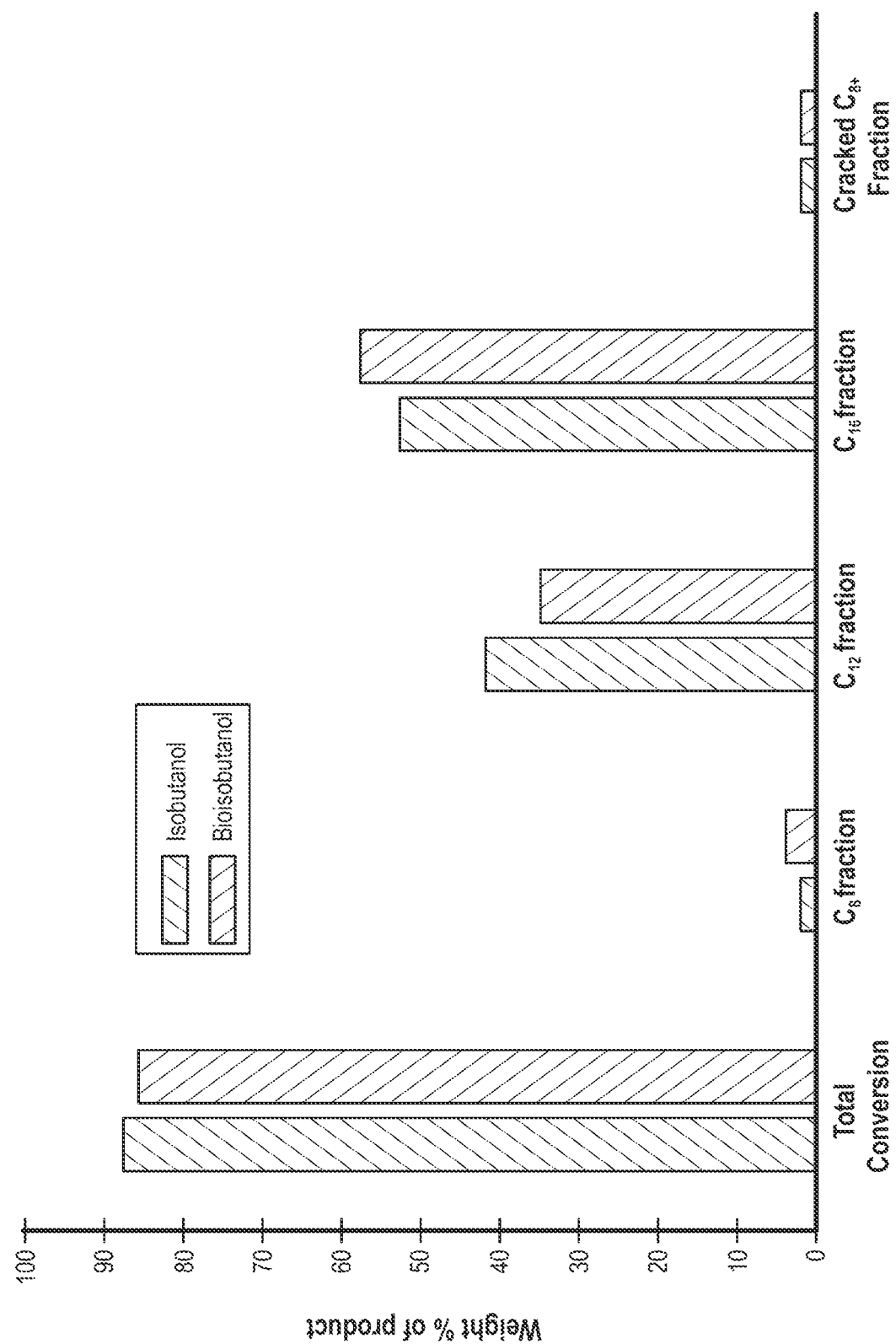
FIG. 10 is a bar graph comparing the product distribution obtained when converting isobutanol or bioisobutanol by a zeolite solid acid catalyst having a MWW framework.

FIG. 10 shows a bar graph of the product distribution obtained from isobutanol in comparison to isobutanol spiked with various impurities. The comparable product distributions suggest that the presence of the impurities in the bioisobutanol did not impact the conversion of the bioisobutanol significantly. Further, conversion still favors $C_{12}$ and $C_{16}$ olefin oligomers while minimizing cracking reactions.

Example 4. Conversion of Isobutanol Under Varying Reaction Conditions

Conversion reactions were performed as described in Example 1. The feed was isobutanol ("IBA") or isobutanol having the impurities as shown in Table 1 ("Blend"). Feed was introduced into the reactor (operated at a pressure of 750 psig (5.17 MPa)) as a continuous stream for more than 1500 hours. Periodically, the operating conditions were changed to match conditions as outlined below in Table 2.

TABLE 2

| Condition | Feed | Temperature (° C.) | LHSV (hour$^{-1}$) | Water (mL) |
|---|---|---|---|---|
| 1 | IBA | 180 | 1 | 0 |
| 2 | IBA | 180 | 1 | 0.78 |
| 3 | IBA | 190 | 1 | 0 |
| 4 | IBA | 180 | 1 | 0 |
| 5 | IBA | 190 | 0.5 | 0 |
| 6 | Blend | 190 | 1 | 0 |
| 7 | Blend | 180 | 1 | 0 |
| 8 | IBA | 180 | 0.5 | 0 |

Figure 11:
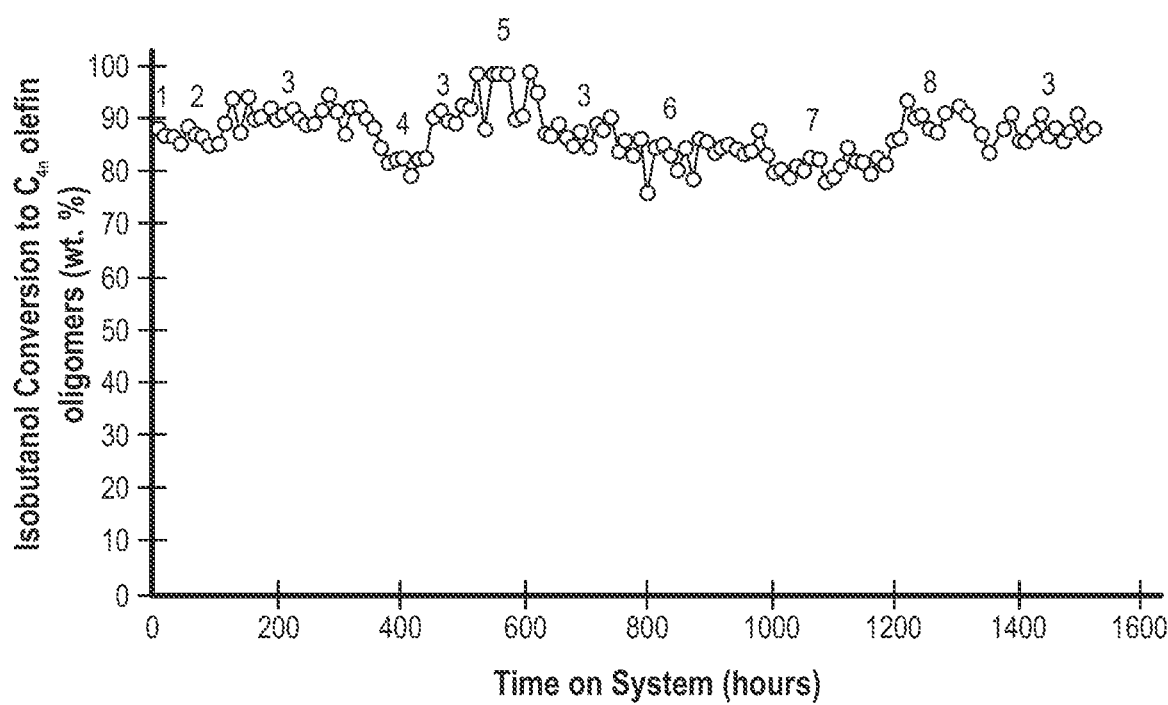
FIG. 11 is a graph illustrating the stability of MCM-49 catalyst over time and under varying reaction conditions.

FIG. 11 illustrates the conversion of the isobutanol in the feed to product over the 1500 hours of running time. Numbers corresponding to the operating conditions in Table 2 indicate when the operating conditions were changed. As shown, stable operation was achieved under the different reaction conditions.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

All numerical values within the detailed description and the claims herein are modified by "about" or "approximately" with respect to the indicated value, and take into account experimental error and variations that would be expected by a person having ordinary skill in the art. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

What is claimed is:

1. A method comprising:
contacting a feed comprising isobutanol with a zeolite solid acid catalyst having an MWW framework under conditions effective to convert the isobutanol into a product comprising $C_{4n}$ olefin oligomers, wherein n is an integer having a value of two or greater and about 80 wt. % or greater of the $C_{4n}$ olefin oligomers are larger than $C_8$.

2. The method of claim 1, wherein about 90 wt. of the $C_{4n}$ olefin oligomers are larger than $C_8$.

3. The method of claim 1, wherein the zeolite solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and any combination thereof.

4. The method of claim 1, wherein the zeolite solid acid catalyst is MCM-49.

5. The method of claim 1, wherein the isobutanol is biologically derived.

6. The method of claim 5, wherein the isobutanol is formed as a byproduct of producing bioethanol.

7. The method of claim 1, wherein the feed further comprises one or more fermentation byproducts.

8. The method of claim 7, wherein the one or more fermentation byproducts comprise at least one member selected from the group consisting of ethanol, xylose, furfural, lactic acid, 5-hydroxymethylfurfural, and any combination thereof.

9. The method of claim 1, wherein the contacting is performed in an absence of co-fed water.

10. The method of claim 9, wherein the product comprises at least about 45 wt. % $C_{12}$ olefin oligomers.

11. The method of claim 9, wherein the product comprises at least about 30 wt. % $C_{16}$ olefin oligomers.

12. The method of claim 1, wherein the product comprises $C_8$ olefin oligomers and at least about 80 wt. % of the $C_8$ olefin oligomers are di branched.

13. The method of claim 1, wherein less than about 0.1 wt. % of the isobutanol is converted into $C_{3-}$ hydrocarbons.

14. The method of claim 1, further comprising:
hydrogenating the $C_{4n}$ olefin oligomers to form $C_{4n}$ isoparaffins.

15. The method of claim 14, wherein formation of the Can olefin oligomers and hydrogenation of the $C_{4n}$ olefin oligomers take place in a single reactor, the feed being contacted with the zeolite solid acid catalyst in an upstream portion of the single reactor and the $C_{4n}$ olefin oligomers being contacted with a hydrogenation catalyst in a downstream portion of the single reactor.

16. The method of claim 14, wherein the formation of the $C_{4n}$ olefin oligomers and hydrogenation of the $C_{4n}$ olefin oligomers take place in separate reactors.

17. The method of claim 1, further comprising:
recycling unconverted isobutanol to the feed.

18. The method of claim 1, wherein the conditions effective to convert the isobutanol comprise one or more of a temperature of about 100° C. to about 300° C., a pressure ranging from atmospheric pressure up to about 1000 psig, and a liquid hourly space velocity (LHSV) of about 0.25 hour-1 to about 6 hour-1.

19. The method of claim 1, wherein contacting takes place in a fixed catalyst bed reactor, a batch reactor, a slurry reactor, or a fluidized bed reactor.

20. The method of claim 1, further comprising:
processing the $C_{4n}$ olefin oligomers into a jet fuel.

* * * * *